United States Patent [19]

Le-Si

[11] Patent Number: 5,296,453
[45] Date of Patent: Mar. 22, 1994

[54] PROCESS FOR THE INTERCONVERSION OF TWO SEPERATE CRYSTAL FORMS OF A HERBICIDAL PYRIDINE SULFONAMIDE

[75] Inventor: Ngoc Le-Si, Greenville, Del.

[73] Assignee: E. I. du Pont de Nemours and Company, Wilmington, Del.

[21] Appl. No.: 997,611

[22] Filed: Dec. 23, 1992

Related U.S. Application Data

[60] Division of Ser. No. 675,933, May 8, 1991, Pat. No. 5,202,439, which is a continuation-in-part of Ser. No. 274,463, Nov. 12, 1988, abandoned.

[51] Int. Cl.$^5$ .................... A01N 43/54; C07D 401/12
[52] U.S. Cl. ..................................... 504/243; 544/320
[58] Field of Search ........................................ 504/243

[56] References Cited

U.S. PATENT DOCUMENTS

| | | | |
|---|---|---|---|
| 4,435,206 | 3/1984 | Levitt | 71/92 |
| 4,518,776 | 5/1985 | Meyer | 544/206 |
| 4,521,597 | 6/1985 | Kristinsson | 544/3 |
| 4,544,401 | 10/1985 | Levitt | 71/92 |
| 4,789,393 | 12/1988 | Hanagan | 544/320 |

FOREIGN PATENT DOCUMENTS

| | | |
|---|---|---|
| 101670 | 2/1984 | European Pat. Off. . |
| 0237292 | 8/1987 | European Pat. Off. . |
| 0232067 | 12/1987 | European Pat. Off. . |
| 0298752 | 1/1989 | European Pat. Off. . |

OTHER PUBLICATIONS

Kimura, CA 108:21919v 1987.
Hanagan, CA 108:75417y 1987.

*Primary Examiner*—Richard L. Raymond
*Assistant Examiner*—B. Bembenick

[57] ABSTRACT

This invention relates to the interconversion of separate crystal forms of (aminosulfonyl)pyridinecarboxamides. The compounds of this invention and their agriculturally suitable salts are useful as agricultural chemicals, and in particular, as herbicides which may be selective to corn.

5 Claims, No Drawings

PROCESS FOR THE INTERCONVERSION OF TWO SEPERATE CRYSTAL FORMS OF A HERBICIDAL PYRIDINE SULFONAMIDE

This is a division of application Ser. No. 07/675,933 filed May 8, 1991 (now U.S. Pat. No. 5,202,439) which was filed as PCT international application number PCT/US89/05052 filed Nov. 17, 1989 a continutation-in-part of Ser. No. 07/274,463 filed Nov. 12, 1988 (abandoned).

BACKGROUND OF THE INVENTION

This invention relates to the interconversion of separate crystal forms of (aminosulfonyl)pyridinecarboxamides. The compounds of this invention and their agriculturally suitable salts are useful as agricultural chemicals, and in particular, as herbicides which may be selective to corn.

U.S. Pat. No. 4,544,401 and U.S. Pat. No. 4,435,206 disclose herbicidal pyridinesulfonylureas.

U.S. Pat. No. 4,518,776 (Swiss priority Jul. 19, 1982) and EP-A-101,670 (Swiss priority Aug, 23, 1982, published Feb. 29, 1984) disclose, in part, a process for the preparation of the compounds of the invention.

U.S. Pat. No. 4,518,776 generically discloses the compound of the invention.

U.S. Pat. No. 4,521,597 discloses, in part, a process for the preparation of the compound of the invention.

SUMMARY OF THE INVENTION

It has been found that preparation of 2[[(4,6-dimethoxypyrimidine-2-yl)aminocarbonyl]-aminosulfonyl-N-N-dimethyl-3-pyridinecarboxamide (Compound I) results in two separate and distinctly different crystal lattice forms (Compounds Ia and Ib) depending on the conditions of preparation.

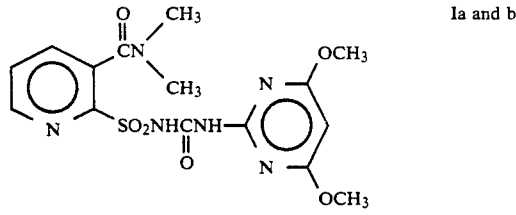
Ia and b

The compound of Formula Ia may be prepared as a non-hygroscopic, anhydrous crystalline solid via a non-aqueous reaction sequence. The compound of Formula Ia in this physical state is uniquely stable and does not absorb water upon standing.

The compound of Formula Ib may be prepared via an aqueous reaction sequence. This well result in the separate distinct crystal form of Formula Ib which is now susceptible upon standing to conversion to the compound of Formula II via water of hydration.

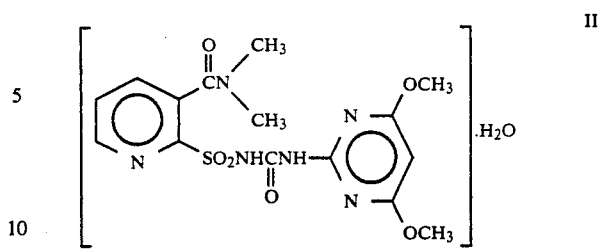

Both crystalline forms are interchangeable by either reaction with water or thermally induced water removal and recrystallization. The compounds of Formula Ia are useful as a stable analytical product and as an intermediate to the compound of Formula Ib. The compound of Formula Ib provides a better water dispersible granuler than Compound Ia when formulated as a dry flowable. Therefore, Compound Ib is the compound of choice for such formulations.

DETAILS OF THE INVENTION

Compounds of Formula Ia and Ib can be prepared by the methods described in Equations 1 and 2.

Equation 1

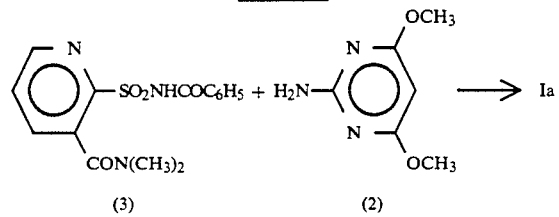

The reaction shown in Equation 1 is carried out by contacting the phenyl carbamate of Formula (3) with the aminoheterocycle of Formula (2) in an inert organic solvent such as dioxane or tetrahydrofuran at temperatures of about −20° to 100° C. for a period of about one-half to twenty-four hours. The product can be isolated by evaporation of the reaction solvent and purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

Equation 2

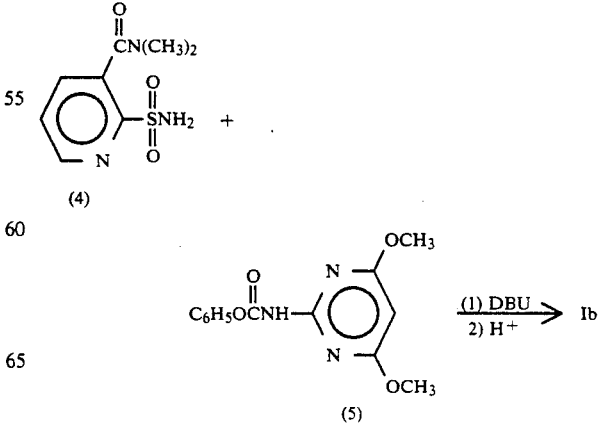

The reaction of Equation 2 can be carried out by contacting equimolar amounts of the sulfonamide of Formula (4) with a heterocyclic phenyl carbamate of Formula (5) in the presence of an equimolar amount of 1,8-diazabicyclo[5.4.0]undec-7-ene (DBU), by methods known to one skilled in the art and analogous to those described in South African Patent Application 830441.

The hydrated form of Ib, that is Compound II, may be prepared from either Ia or Ib. Slurrying a solution of Ia in water and an appropriate organic solvent such as ethyl acetate heating results in the direct conversion to Compound II. Compound II may be converted to Ib via removal of the solvent and water by thermal evaporation of the solvent and water. Compound Ib may then be converted to Ia by dissolving in the appropriate organic solvent such as ethyl acetate and allowing it to crystallize under anhydrous conditions. The above sequence is outlined in equation 3.

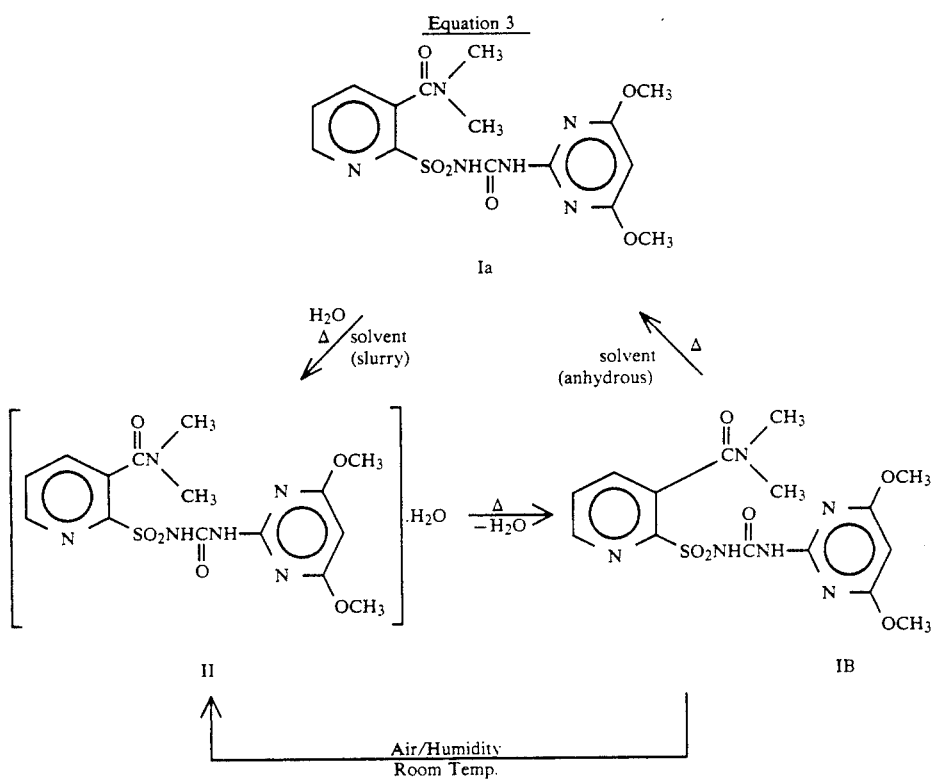

The following examples further illustrate the process of the invention.

EXAMPLE 1

N,N-Dimethyl-2-[[4,6-dimethoxypyrimidin-2-yl)aminocarbonyl]aminosulfonyl]-3-pyridinecarboxamide (Ib)

To a suspension of 0.50 g (2.2 mmol) N,N-dimethyl-2-(aminosulfonyl)-3-pyridinecarboxamide and 0.60 g (2.2 mmol) of 4,6-dimethoxypyrimidin-2-yl phenyl carbamate in 3 ml acetonitrile was added 0.32 ml (2.2 mmol) of 1,8-diazabicyclo[5.4.0]undec-7-ene (DBU). The resulting solution was stirred at room temperature for 7 minutes. The addition of 6 ml of water followed by the dropwise addition of 10% hydrochloric acid produced a white precipitate which was collected by filtration to provide 0.75 g of the subject compound, m.p. 142°–159° C.(d). IR (Nujol) 1720 (CO), 1609, 1365, 1162 cm$^{-1}$.

EXAMPLE 2

N,N-Dimethyl-2-[[4,6-dimethoxypyrimidin-2-yl)aminocarbonyl]aminosulfonyl]-3-pyridinecarboxamide (Ia)

12.0 parts of the phenyl carbamate of the pyridine sulfonamide, 5.33 parts of 2-amino-4,6-dimethoxypyrimidine, and 36 parts of ethyl acetate were refluxed for 1.0 hour. The slurry was cooled and filtered. The solids were washed with ethyl acetate and dried to give 12.3 parts (87.3% yield) of the subject compound, m.p. 184°–185° C.

EXAMPLE 3

Preparation of Compound Ia and conversion to Compound Ib.

The phenyl carbamate of the pyridine sulfonamide (90 parts) was added during 30 minutes to a solution of 41.7 parts of 2-amino-4,6-dimethoxypyrimidine in 486 parts of ethyl acetate. The temperature was kept at approximately 70° C. during the addition. The resulting slurry was then refluxed for 2 hours. After the 2 hour reflux period 9 parts of water were added. After cooling the slurry, the product, which was now in the form of its monohydrate (Compound II) was collected by filtration and washed with ethyl acetate. Drying under vacuum at 80° C. removed the water of hydration and gave 90.5 parts of Compound Ib. The proton NMR spectra of the two crystal forms of Ia and Ib were identical in acetone solution or DMSO solutions. NMR (200 MHz, DMSO) δ 30 (d, 6H); 3.97 (s, 6H); 5.9 (s, 1H); 7.8 (d, d, 1H); 8.0 (d, d, 1H); 8.7 (d, 1H); 9.5 (br, s, 1H); 12.8 (br, s, 1H).

EXAMPLE 4

Preparation of Compound Ia from Compound Ib.

6.5 grams of Compound Ib and 26.0 ml of anhydrous ethyl acetate were added to a 100 ml, round bottom flask. The reaction solution was heated to 76° C., and refluxing was continued for 1 hour at 76° C. After 1 hour, an addition of 20 ml of ethyl acetate was made to provide a thinner slurry in the flask and heating was continued for another hour. The solution was cooled and then filtered. The solids were dried in the vacuum oven at 70° C. A sample was then submitted to an X-ray powder diffraction analysis which showed a mixture of Compounds Ia and Ib. The NMR of both Compounds Ia and Ib were identical as follows: NMR (200 MH3,DMSO) 3.0(d,6H); 3.97(s,6H); 5.9(s,1H); 7.8(d,d,1H); 8.0(d,d,1H); 8.7(d,1H); 9.5(br,s,1H); 12.8(br,s,1H).

The thermal properties of both compounds of Example 1 and Example 2 were determined via Differential Scanning Calorimetry (DSC).

All thermal data were collected on a Du Pont Model 1090 Thermal Analyzer from ambient to 200° C. The Model 1090 was connected to a Du Pont Model 910 DSC Module for the differential scanning calorimetry experiments. The DSC Module was purged with nitrogen during the course of the experiments. Prior to the experiments, the DSC Module was calibrated using pure indium.

For the DSC work, approximately 2 mg of each sample was hermetically sealed into a coated aluminum sample pan. The sample was then heated from ambient to 200° C. at a rate of 5° C./minute. Following each scan, the data was plotted and analyzed using the 1090 General Analysis program (v1.0). The analysis was repeated 3 times using different samples for each run.

| Group | Compound | Approx. H$_2$O Content | Temperature of Thermal Events |
|---|---|---|---|
| A | Ib | 0.47% | 125.7 (small) |
|   |    |       | 169.3 (large) |
|   | Ia | 0.23% | 169.4 (large) |
| B | Ib[1] | 4.3% | 131.0 (large) |
|   | Ia | — | — |
| C | Ib | 0.40% | 123.3 (large) |
|   | Ia | 0.14% | 172.3 (large) |

[1]Prepared from Ia of Group A via an aqueous slurry.

In addition to DSC, Compounds Ia and Ib were further differentiated by x-ray powder diffraction;
Philips automated powder diffractometer model 3600-02
Theta compensating slit and graphite monochromater
Copper (K-alpha) radiation, 40 kV, 30 mA
Step size: 0.03 degree 2-theta
Count time: 1.0 second
Maximum peak intensity: 1989 counts per second
Scan range: 2–60 degrees 2-theta

| Compound Ia | | | Compound Ib | | |
|---|---|---|---|---|---|
| 2-Θ Deg. | d Ang. | I I/I$_o$ | 2-Θ Deg. | d Ang. | I I/I$_o$ |
| 5.592 | 15.80 | 4 | 10.195 | 8.677 | 28 |
| 6.930 | 12.76 | 41 |  |  |  |
| 8.898 | 10.66 | 12 | 13.230 | 6.692 | 100 |
| 9.013 | 9.812 | 14 | 14.066 | 6.296 | 26 |
| 11.425 | 7.745 | 33 |  |  |  |
| 12.194 | 7.258 | 19 | 15.387 | 5.759 | 23 |
|  |  |  | 17.973 | 4.936 | 5 |
| 14.003 | 6.324 | 100 | 19.084 | 4.651 | 11 |
|  |  |  | 20.411 | 4.351 | 34 |
|  |  |  | 21.014 | 4.228 | 6 |
| 15.311 | 5.787 | 32 | 21.796 | 4.078 | 5 |
| 16.769 | 5.287 | 23 | 22.512 | 3.950 | 13 |
| 18.149 | 4.889 | 42 | 23.306 | 3.817 | 25 |
| 18.543 | 4.785 | 25 |  |  |  |
|  |  |  | 25.661 | 3.472 | 85 |
| 19.161 | 4.632 | 11 |  |  |  |
|  |  |  | 26.426 | 3.373 | 15 |
| 20.154 | 4.406 | 9 | 27.341 | 3.262 | 19 |
| 21.700 | 4.096 | 42 | 27.993 | 3.188 | 29 |
| 23.198 | 3.834 | 35 |  |  |  |
| 23.816 | 3.736 | 50 |  |  |  |
| 24.614 | 3.617 | 37 |  |  |  |
| 25.263 | 3.525 | 74 |  |  |  |
| 25.776 | 3.457 | 39 |  |  |  |
| 26.555 | 3.357 | 28 |  |  |  |
| 26.954 | 3.308 | 19 |  |  |  |
| 27.450 | 3.249 | 22 |  |  |  |
| 28.337 | 3.150 | 36 |  |  |  |

As can be seen, the two compounds give separate and distinct x-ray diffraction patterns, clearly indicating distinct crystal lattice structures.

EXAMPLE 5

Moisture Pick-Up Test

The propensity of moisture absorption of Compounds Ia and Ib was determined as follows:

The 2 samples were placed in 50 and 90% relative humidity chambers. After a given time, the moisture of each sample was determined. The moisture check was continued until no further increase in moisture was observed. Results are summarized below:

a. Initial moisture in samples: (by Karl Fischer method)
1. Compound Ib: 0.47% water
2. Compound Ia: 0.23% water b. Samples in 50 and 90% RH chambers:

| Humidity Chambers Time | Compound Ib | | Compound Ia | |
|---|---|---|---|---|
|  | 50% RH % Water | 90% RH Absorbed | 50% RH % Water | 90% RH Absorbed |
| 4 hrs | 5.0 | 4.8 | 1.0 | 0.9 |
| 6.5 hrs | 3.8 | 4.3 | 0.6 | 0.2 |
| 19 hrs | 4.4 | 4.3 | 0.2 | 0.3 |
| 24 hrs | 4.3 | 4.3 | 0.2 | — |
| initial | — | — | 0.23 | 0.23 |
| 1 day | — | — | — | 0.3 |
| 4 days | — | — | — | 1.2 |
| 8 days | — | — | 0.16 | 4.0 |

As seen above, Compound Ia is not hygroscopic under normal conditions (only 0.2% moisture) while the hygroscopic Compound Ib has absorbed 4.3% water. This 4.3% water is approximately equivalent to 1 mole of water per mole of Compound.

Formulations

Useful formulations of the compounds of Formula Ia, Ib and II can be prepared in conventional ways. They include dusts, pellets, solutions, suspensions, emulsions, wettable powders, emulsifiable concentrates and the like, in particular the compounds of Formula Ia, Ib and II may be formulated as granules. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

|  | Active Ingredient | Weight Percent Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength | 90-99 | 0-10 | 0-2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All Formulations can contain minor amounts of additives to reduce foaming, caking, corrosion, microbiological growth, and the like.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084 Granules and pellets may be made by spraying the active material upon preformed granular carriers or by agglomeration techniques. See Browning, Agglormeration, *Chemical Engineering*, Dec. 4, 1967, pp. 147ff. and "Perry's Chemical Engineer's Handbook", 5th Ed., McGraw-Hill, New York, 1973, pages 8 to 57 and following.

For further information regarding the art of formulation, see in particular U.S. Pat. No. 3,920,442 or for additional information see for example: U.S. Pat. No. 3,235,361, Column 6, line 16 through column 7, line 19 and Examples 10 through 41; U.S. Pat. No. 3,309,192, column 5, line 43 through column 7, line 62 and Examples 8, 12, 15, 39, 41, 52, 53, 58, 132, 138 to 140, 162 to 164, 166, 167 and 169 to 182; U.S. Pat. No. 2,891,855, column 3, line 66 through column 5, line 17 and Examples 1 to 4; Klingman, "Weed Control as a Science", John Wiley and Sons, Inc., New York, 1961, pages 81 to 96; and Fryer et al., "Weed Control Hand-book", 5th Ed., Blackwell Scientific Publications, Oxford, 1968, pages 101 to 103.

The following example exemplifies the preparation of a dry flowable formulation and the superior properties of Compound Ib.

EXAMPLE 6

| | Granule | Weight % | Purpose |
|---|---|---|---|
| 1. | Compound Ia or Ib | 75.00 | Active ingredient |
| 2. | Siponate DS-10 | 3.50 | Wetting Agent |
| 3. | Lomar PWM | 4.00 | Dispersing Agent |
| 4. | Morwet D-425 | 3.50 | Dispersing Agent |
| 5. | Sugar | 1.50 | Binding Agent |
| 6. | 1432 Kaolin Clay | 12.50 | Diluent |

Description of Granulation Equipment and Process

The powder is charged to the conical air expansion section of a fluidized bed agglomerator which consists of 5 principal sections:

1. A lower conical air expansion section, 9 inches long, increasing from 1 inch diameter at the bottom end to 3 inches diameter at the upper end and fitted at the bottom with an air inlet chamber 2 inches long by 1 inch diameter. The air inlet chamber is provided with a mean to admit fluidizing air. The air inlet chamber and expansion section are made of stainless steel.
2. A fluidizing section connected to the air expansion section in such a manner that no air escapes between adjacent sections, consisting of a "Lucite" acrylic tube 3-inch O.D.×2¾ inch I.D.×7 inches long, is mounted coaxially immediately above the expansion section.
3. A second expansion section, 3 inches in diameter at the lower end and 6 inches in diameter at the upper end, and 7 inches long, made of stainless steel, is mounted above and coaxially with the fluidizing section.
4. A spraying/disengaging section to permit spraying of the fluidized powder and separation of the fluidized air and the agglomerated powder, made of "Lucite" 6-inch O.D.×5¼ inch I.D., is mounted and coaxially with the upper expansion section. For the atomization of water onto the fluidizing powder, a DeVilbiss No. 152 spray nozzle is used. The nozzle is inserted into the side hole of the spraying/disengaging section and its spray tip positioned at the center and downward to the fluidized bed. Air at 20 psig is connected to the air inlet of the atomizer while the liquid inlet is connected to a reservoir of water.
5. A cylindrical dust filter, 6-inch diameter by 14 inches long, sealed at the upper end, made of fiber reinforced fabric, is attached to the top of the disengaging section in such a manner that the air is forced to pass through the filter before escaping into a fume hood.

The entire assembly is rigidly mounted with the axis vertical and arranged with the air inlet chamber at the lower end and the filter uppermost. The entire assembly is about 35 inches long. Fluidizing air is admitted to the air inlet chamber at about 8-10 psig and the powder gently fluidized. Fluidizing air pressure is gradually raised to 15 psig during the addition of water. Water added to the process is 30-35% by weight of the powder. During the agglomeration process, the powder, which has been brought to a fluidized state, receives the fine water mist from the spray nozzle and is subsequently converted to aggregates (also called granules). At the end of the spray cycle begins the drying cycle where wet granules are dried by the same inlet air that is now heated to the desired temperature in the air heater. Dried granules are then checked for their water-dispersibility.

Water-Dispersibility Test

The test measures the degree of dispersibility of granules in distilled water. One gram of the material to be tested is placed in a 30 ml. tall form "Pyrex" beaker containing 20 ml. of distilled water, and stirred for 60 seconds using a "Teflon" polytetrafluoroethylene coated magnetic stirring bar ¼ inch dia.×1 inch long, driven by a magnetic stirrer at 30 r.p.m. The stirrer is stopped and the stirring bar removed and rinsed with a small stream of distilled water, using approximately 1 ml of water. The suspension or dispersion is immediately and quickly poured into the assembled settling tube containing 200 ml. of distilled water, rinsing all solids from the beaker with a small stream of distilled water, using 3-5 ml.

The settling tube assembly consists of a 6.5 ml. centrifuge tube graduated from the lower end tip of 0.4 ml. in 0.01 ml. divisions (A. H. Thomas Co., Philadelphia, Pa., "Cat. No. 2998-655" or equivalent) with the neck consisting of the female part of a 19/22 standard taper joint. The male half of the taper joint is attached to the lower end of a long open Pyrex tube 19 mm. O.D.×17 mm. I.D. and inserted into the female half of the centrifuge tube. The assembly is about 1030 mm. from the tip of the centrifuge tube to the upper end of the open Pyrex tube. The Pyrex tube is marked to correspond to 200 ml. total volume, about 900+ −25 mm. from the tip of the centrifuge tube. The assembly is held so that the longitudinal axis is vertical, before the tube is filled to the 200 ml. mark with distilled water. The rate of settling of the suspended solids and the volume of settled solids is noted 1, 3, and 5 minutes after pouring the suspension or dispersion into the settling tube assembly. Excellent dispersibility is observed when the volume of settled solids after 5 minutes is less than about 0.01 ml., although acceptable dispersibility is observed for materials which show a volume of settled solid of about 0.01 ml. after 5 minutes.

| Water Dispersibility Test Results | | |
|---|---|---|
| Compound | Conditions (history) of Samples | Water-Dispersibility (ml) |
| Ia | As made | 0.002-0.04 |
| Ib | As made | >0.002 |
| Ia | Heated in 55° C. oven for 2 weeks | >0.02 |
| Ib | Heated in 55° C. oven for 2 weeks | <0.002 |
| Ia | Heated in 45° C. oven for 3 weeks | >0.02 |
| Ib | Heaed in 45° C. oven for 3 weeks | <0.002 |

Utility

Corn (maize) is a very important cereal crop, providing animal feed as well as food for human consumption. As will all crops, high yields depend on good control of unwanted plants to minimize competitive effects on the crop. Since corn is a grass, it is particularly difficult to control other grasses competing with the crop. Many of the compounds of this invention control weeds in corn both pre- and postemergence without significant crop damage. Such compounds are particularly useful to control such problem weeds as the foxtail (*Setaria spp.*), fall panicum (*Panicum dichotomiflorum*), barnyardgrass (*Echinochloa crusgallis*), seedling johnsongrass (*Sorghum halepense*) and shattercane (*Sorghum bicolor*). They can be used pre-emergence or postemergence and are most effective when applied postemergence to young weeds. They are also effective on certain broadleaf weeds such as lambsquarter (*Chenopodium album*), pigweed (*Amaranthus spp.*) and jimsonweed (*Datura stramonium*). The rate used can vary from about 0.5 g/ha to 1000 g/ha depending on the number and age of weeds present, soil type, climate, formulation used and method of application. One of ordinary skill in the art can readily select the exact rate and method of application that will provide the desired herbicidal efficacy.

The utility of these chemicals is demonstrated in terms of the greenhouse test data summarized hereafter. The results demonstrate the herbicidal efficacy and corn selectivity of the compounds of this invention.

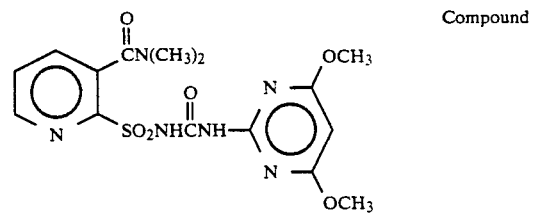

Compound

Test A

Seeds of crabgrass (*Digitaria sp.*), barnyard-grass (*Echinochloa crusgalli*), giant foxtail (*Setaria faberi*), wild oats (*Avena fatua*), cheatgrass (*Bromus secalinus*), velvetleaf (*Abutilon theophrasti*), morningglory (*Ipomoea spp.*), cocklebur (*Xanthium pensylvanicum*), sorghum, corn, soybean, sugarbeet, cotton, rice, wheat, barley and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;

U = unusual pigmentation;
X = axillary stimulation;
S = albinism; and
6Y = abscised buds or flowers.

TABLE A

|  | Compound Ib | |
| --- | --- | --- |
| Rate = Kg/Ha Postemergence | 0.01 | 0.05 |
| Cotton | 9H | 4C, 9H |
| Morningglory | 9C | 10C |
| Cocklebur | 4G | 3C, 8G |
| Nutsedge | 9G | 2C, 9G |
| Crabgrass | 7G | 4C, 9G |
| Barnyardgrass | 5C, 9G | 9C |
| Wild Oats | 3C, 9G | 3C, 9G |
| Wheat | 8G | 3C, 9G |
| Corn | 0 | 2G |
| Soybean | 4H | 4C, 8H |
| Rice | 5C, 9G | 5C, 9G |
| Sorghum | 5C, 9G | 9C |
| Cheatgrass | 4C, 9G | 4C, 9G |
| Sugar Beets | 5C, 9G | 5C, 9G |
| Velvetleaf | 3C, 7H | 9C |
| Giant Foxtail | 5C, 9G | 9C |
| Barley | 4C, 9G | 5C, 9G |
| Rate = Kg/Ha Preemergence | | |
| Cotton | 5G | 8H |
| Morningglory | 5H | 9G |
| Cocklebur | 3G | — |
| Nutsedge | 8G | 10E |
| Crabgrass | 2G | 3G |
| Barnyardgrass | 7G | 9H |
| Wild Oats | 2C, 3G | 3C, 8H |
| Wheat | 8G | 9H |
| Corn | 0 | 4G |
| Soybean | 0 | 3G |
| Rice | 9H | 10E |
| Sorghum | 3C, 9H | 5C, 9H |
| Cheatgrass | 5G | 9H |
| Sugar Beets | 3C, 7G | 4C, 9G |
| Velvetleaf | 2G | 7G |
| Giant Foxtail | 8G | 3C, 9H |
| Barley | 8G | 3C, 9G |

What is claimed is:

1. A dry flowable preparation which comprises

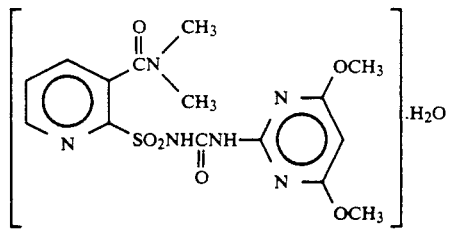

as the active ingredient prepared by hydrating

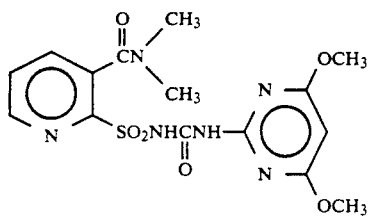

or hydrating

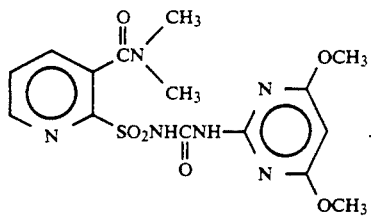

in the presence of heat.

2. An improved dry flowable herbicidal composition comprising 2[[(4,6-dimethoxypyrimidine-2-yl)aminocarbonyl]aminosulfonyl]-N,N-dimethyl-3-pyridinecarboxamide as an active ingredient and at least one of a surfactant and at least one diluent, wherein the improvement comprises use of the crystal lattice form of said active ingredient of Formula Ib

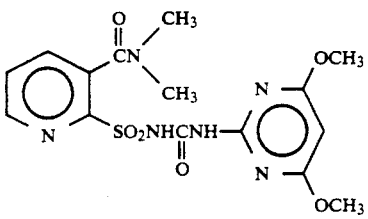

having a water dispersibility of less than about 0.002.

3. An improved dry flowable herbicidal composition comprising 2[[(4,6-dimethoxypyrimidine-2-yl)aminocarbonyl]aminosulfonyl]-N,N-dimethyl-3-pyridinecarboxamide as an active ingredient and at least one of a surfactant and at least one diluent, wherein the improvement comprises use of the crystal lattice form of said active ingredient of Formula II

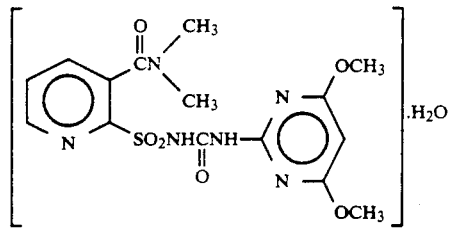

having a water dispersibility of less than about 0.002.

4. An improved dry flowable herbicidal composition comprising 2[[(4,6-dimethoxypyrimidine-2-yl)aminocarbonyl]aminosulfonyl]-N,N-dimethyl-3-pyridinecarboxamide as an active ingredient and at least one of a surfactant and at least one diluent, wherein the improvement comprises use of the crystal lattice form of said active ingredient of a mixture of Formula Ib

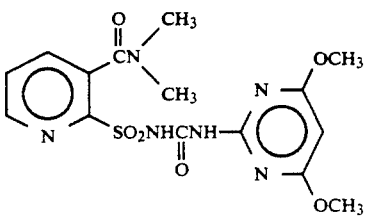

and Formula II

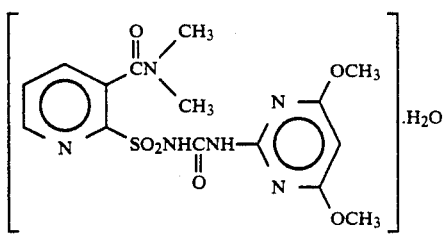

II

.H₂O having a water dispersibility of less than about 0.002.

5. A process for the preparation of an improved dry flowable herbicidal composition of claim 2, 3, or 4 comprising granulizing a compound of Formula Ib, II, or a mixture thereof, in the presence of water and at least one of a surfactant and at least one diluent.

* * * * *

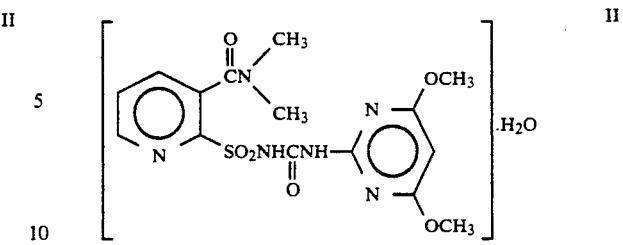

II

.H₂O having a water dispersibility of less than about 0.002.

5. A process for the preparation of an improved dry flowable herbicidal composition of claim 2, 3, or 4 comprising granulizing a compound of Formula Ib, II, or a mixture thereof, in the presence of water and at least one of a surfactant and at least one diluent.

* * * * *